(12) United States Patent
Zhang et al.

(10) Patent No.: US 9,655,619 B2
(45) Date of Patent: May 23, 2017

(54) LINEAR STAPLER

(75) Inventors: Yang Zhang, Shanghai (CN); Shan Wan, Mason, OH (US); Xiangchun Hong, Shanghai (CN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 570 days.

(21) Appl. No.: 14/126,510

(22) PCT Filed: Jun. 7, 2012
(Under 37 CFR 1.47)

(86) PCT No.: PCT/US2012/041319
§ 371 (c)(1),
(2), (4) Date: May 15, 2014

(87) PCT Pub. No.: WO2012/177409
PCT Pub. Date: Dec. 27, 2012

(65) Prior Publication Data
US 2016/0249914 A1    Sep. 1, 2016

(30) Foreign Application Priority Data
Jun. 21, 2011   (CN) .......................... 2011 1 0189677

(51) Int. Cl.
*A61B 17/072*    (2006.01)
*A61B 17/295*    (2006.01)
*A61B 17/29*     (2006.01)

(52) U.S. Cl.
CPC .......... *A61B 17/072* (2013.01); *A61B 17/295* (2013.01); *A61B 2017/2925* (2013.01); *A61B 2017/2946* (2013.01)

(58) Field of Classification Search
CPC .... A61B 17/068; A61B 17/072; A61B 17/295
USPC ............... 227/19, 175.1, 176.1, 178.1, 181.1
See application file for complete search history.

(56) References Cited

U.S. PATENT DOCUMENTS

| 3,494,533 | A | * | 2/1970 | Green | A61B 17/072 227/155 |
| 4,941,623 | A | * | 7/1990 | Pruitt | A61B 17/072 227/175.1 |
| 5,027,834 | A | * | 7/1991 | Pruitt | A61B 17/072 128/898 |
| 5,137,198 | A | * | 8/1992 | Nobis | A61B 34/74 227/175.3 |

(Continued)

FOREIGN PATENT DOCUMENTS

EP    0539762 A1    5/1993

*Primary Examiner* — Nathaniel Chukwurah

(57) ABSTRACT

The present invention relates to a surgical stapler comprising: a support base; a trigger; a handle; a retaining pin operatively connected to and extending distally from a support base, the support base being operable in the surgical stapler to cause the stapler to position staples near tissue; and a unit lockout rotatable about a pivot fixed to the handle. The unit lockout comprises an upper end near and under at least one blocking plate in the stapler; and another end facing the trigger to prevent it from firing when the upper end is blocked from upward movement by the at least one blocking plate. Whereas the upper end of the unit lockout is moved relative to the at least one blocking plate so that the upper end of unit lockout is no longer under the at least one blocking plate to permit the unit lockout to rotate about the pivot.

11 Claims, 7 Drawing Sheets

(56) References Cited

U.S. PATENT DOCUMENTS

| | | |
|---|---|---|
| 5,579,978 A | 12/1996 | Green et al. |
| 5,810,240 A | 9/1998 | Robertson |
| 2005/0070925 A1 | 3/2005 | Shelton, IV et al. |
| 2008/0314954 A1 | 12/2008 | Boudreaux |

* cited by examiner

LINEAR STAPLER

TECHNICAL FIELD

The present invention relates to a surgical stapling and cutting instrument. More specifically, the present invention relates to a linear stapler incorporating a unit lockout. The unit lockout can effectively prevent the linear stapler from firing when it is not properly aligned with and does not clamp the tissue properly.

BACKGROUND OF THE INVENTION

Surgical stapling and cutting instruments have been used in the prior art to simultaneously make an incision in tissue and apply lines of staples on opposing sides of the incision. End effectors of such instruments commonly include a pair of cooperating jaw members that, if the instrument is intended for endoscopic or laparoscopic applications, are capable of passing through a cannula passageway. One of the jaw members generally receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

It is often advantageous to build a reusable end effector for the surgical stapler. For instance, one patient may need a series of severing and stapling operations. Replacing an entire end effector for each operation tends to be economically inefficient. This is especially true if the end effector is built for strength and reliability for repeated operations. To that end, staple cartridges are fitted into the end effector prior to each operation of the surgical stapler.

While the staple cartridge containing staples provides numerous advantages, it is desirable to prevent inadvertent firing of the instrument when it is not properly aligned with and does not clamp the tissue properly. Moreover, for ease of manufacturing and assembly, it is further desirable that the lockout features be accomplished with a minimum number of components.

Consequently, a significant need exists for improved lockout mechanisms for surgical stapling and cutting instruments, particularly in linear staplers, that prevent firing when the instrument or stapler is not aligned to clamp the tissue properly.

SUMMARY OF THE INVENTION

The present invention relates to a unit lockout adapted for use in a linear stapler and the linear stapler incorporating the unit lockout. The unit lockout can effectively prevent the linear stapler from firing when it is not properly aligned and does not appropriately clamp tissue.

According to an aspect of the present invention, a surgical stapler is provided. The surgical stapler comprises:
a support base;
a trigger located at a proximal end of the support base;
a handle located at a proximal end of the support base;
a retaining pin operatively connected to and extending distally from a support base, the support base being operable in the surgical stapler to cause the stapler to position staples near tissue; and
a unit lockout rotatable about a pivot fixed to the handle, the unit lockout comprising:
an upper end near and under at least one blocking plate in the stapler; and
another end facing the trigger to prevent it from firing when the upper end is blocked from upward movement by the at least one blocking plate,
whereas the upper end of the unit lockout is moved relative to the at least one blocking plate so that the upper end of unit lockout is no longer under the at least one blocking plate to permit the unit lockout to rotate about the pivot.

Preferably, the at least one blocking plate comprises a connect cover plate from which the retaining pin is rigidly connected and extended distally, wherein when the retaining pin is not moved distally the connect cover plate blocks the upper end of the unit lockout from moving upward freely.

Preferably, the at least one blocking plate comprises at least one lockout plate rigidly connected to a support base movable relative to the handle, the upper end of the unit lockout being movable relative to the lockout plate.

Preferably, the at least one blocking plate comprises a connect cover plate from which the retaining pin is rigidly connected and extending distally wherein when the retaining pin is not moved distally the connect cover plate blocks the upper end of the unit lockout from moving upward freely and the at least one blocking plate further comprises at least one lockout plate rigidly connected to a support base which is movable relative to the handle.

Preferably, the unit lockout further comprises a lockout knob located adjacent the another end and capable of being slid downwards in a groove formed in an upper portion of the proximal surface of the handle by a user when the retaining pin is moved distally and the upper end is not blocked from upward movement by the at least one blocking plate, so that the unit lockout can be rotated, allowing the trigger to be rotated towards the handle.

Preferably, the unit lockout is in an L shape, a blunt triangle shape, a crescent shape, or a gusset shape.

Preferably, the unit lockout is made of metal or polymer.

Preferably, the retaining pin extends in a direction about parallel to the direction of slide of a connect cover plate rigidly connected to the retaining pin slidable on the support base but is off set upward from the slidable connect cover plate by 1 cm to 10 cm.

Preferably, the pivot is located at an upper portion of the handle.

Preferably, the retaining pin is connected to a push button via a connect cover plate operatively.

Preferably, when the retaining pin is shifted distally but not properly positioned yet, the unit lockout is rotated an angle smaller than a threshold angle and the trigger cannot be fired, when the unit lockout is rotated continuously as desired by the operator and beyond the threshold angle, the upper end will push the retaining pin to position it properly, so that the trigger can be fired.

BRIEF DESCRIPTION OF THE DRAWINGS

Embodiments of the present invention will be described below with reference to the appended drawings, in which.

EMBODIMENTS

For convenience and ease of understanding, like parts are indicated by like reference signs in the context. It will be appreciated that the terms "proximal" and "distal" are used herein with reference to a user gripping a handle of an instrument. Thus, an end effector is distal with respect to a more proximal handle. It will be further appreciated that, for convenience and clarity, spatial terms such as "vertical" and "horizontal", "up" and "down" are used herein with respect to the drawings. However, surgical instruments are used in many orientations and positions, and these terms are not intended to be limiting and absolute.

Figure 1:
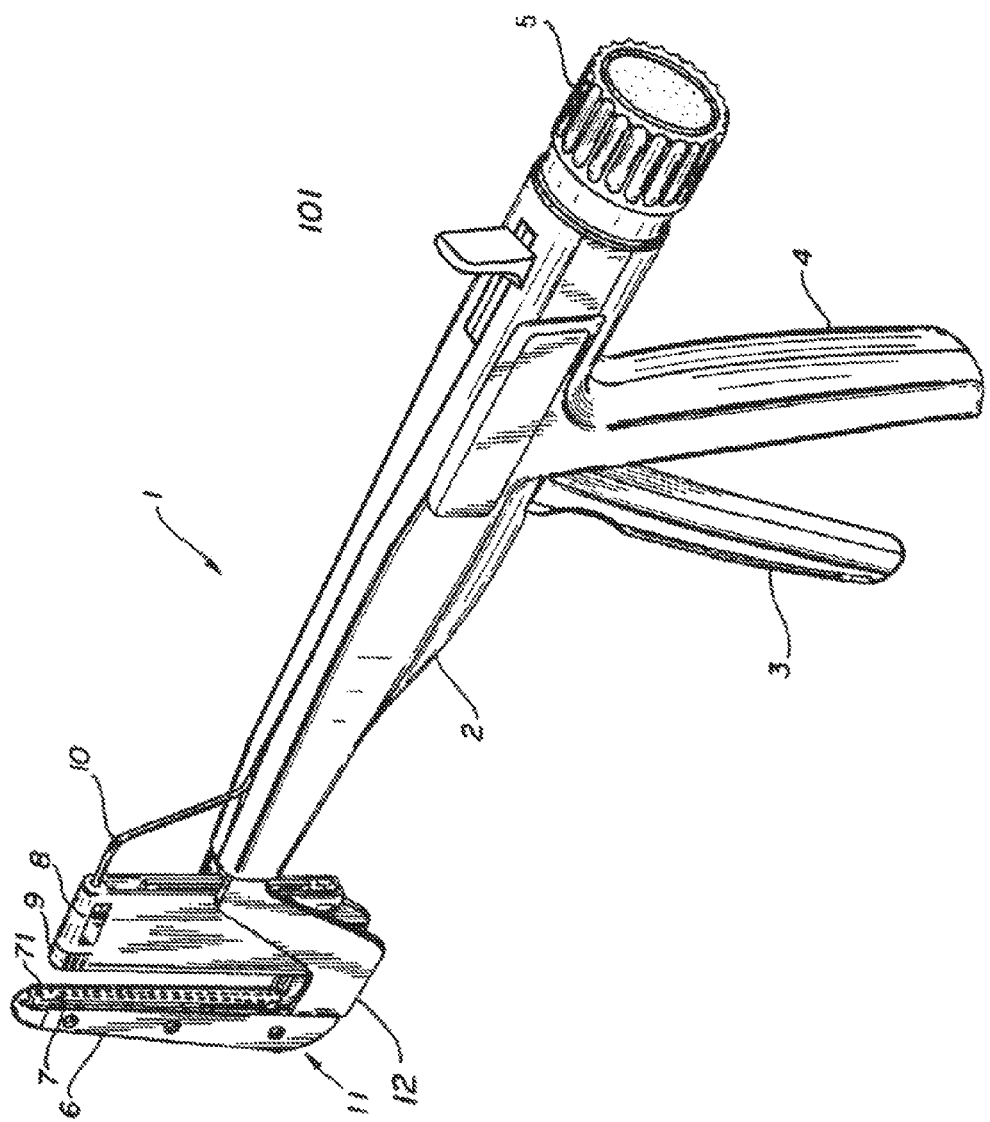
FIG. 1 is a perspective view of a linear stapler in accordance with one embodiment of the present invention.
Figure 2:
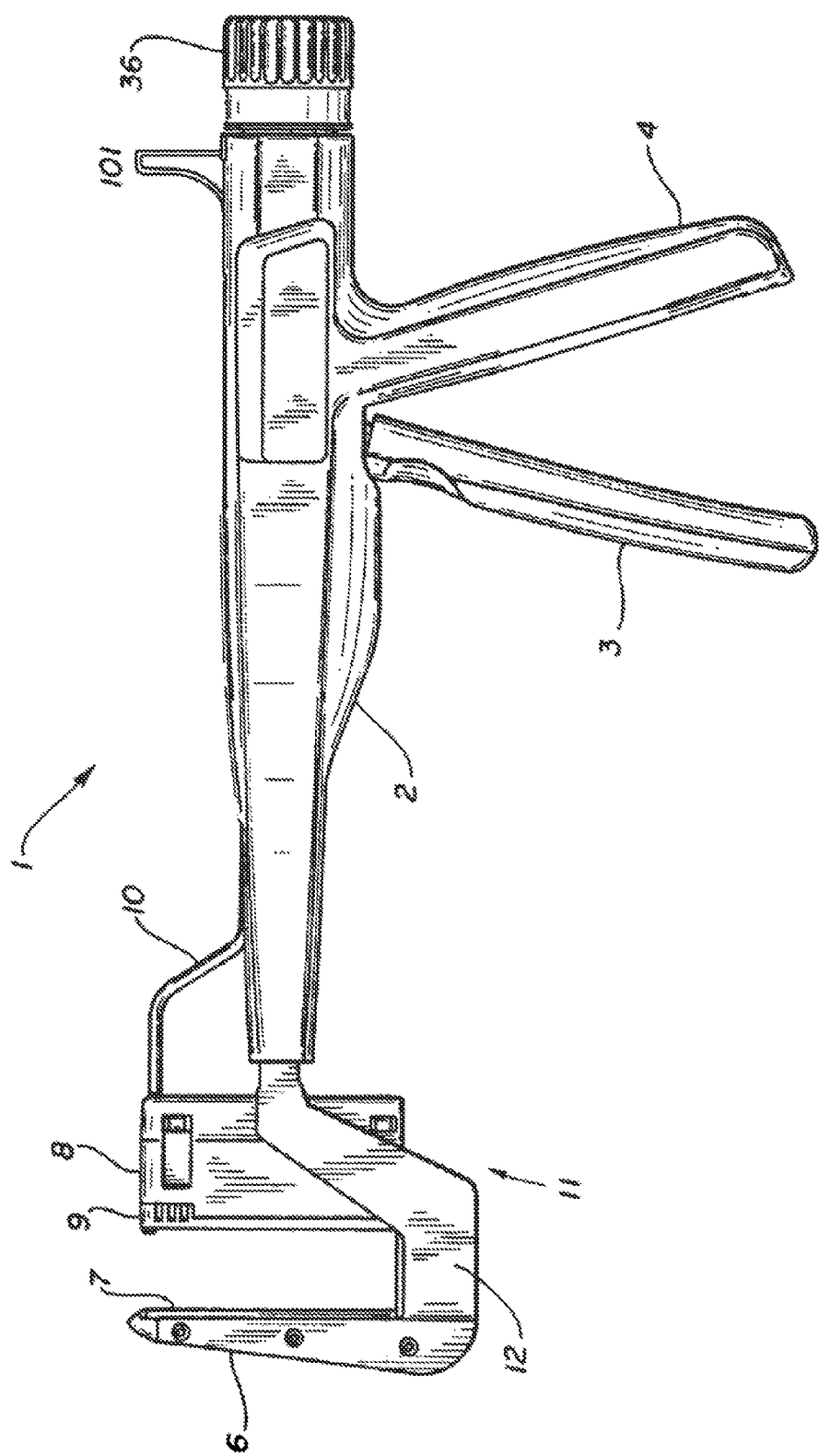
FIG. 2 is a side view of the linear stapler of FIG. 1 in an unactuated open position.
Figure 3:
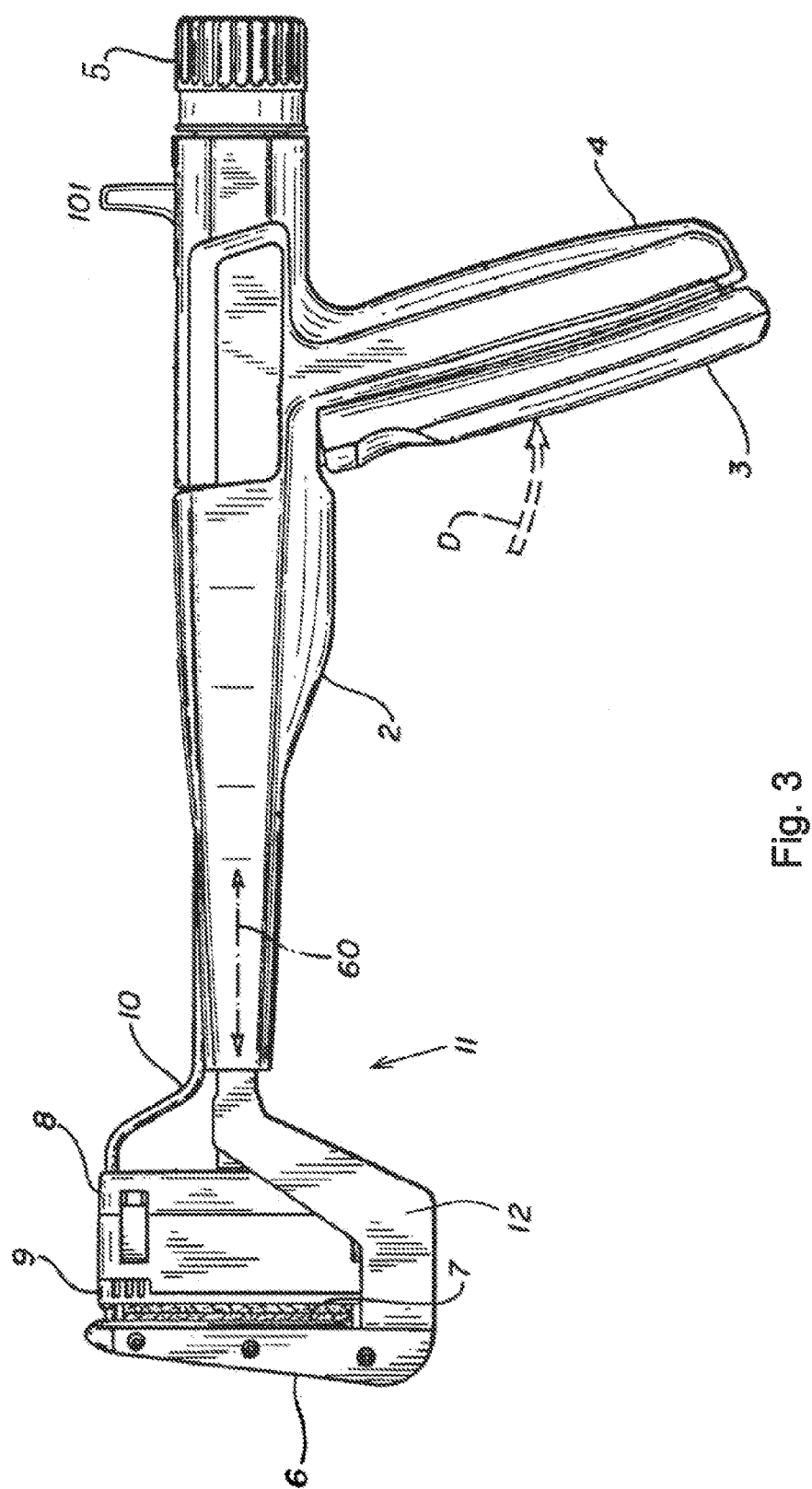
FIG. 3 is a side view of the linear stapler of FIG. 1 in an actuated closed position.

FIG. 1 shows the perspective view of an exemplary stapler 1 according to one embodiment of the present invention. The stapler 1 comprises a support base 2 having a proximal end and a distal end, an end effector 11 located about the distal end of the support base 2, a trigger 3 and a handle 4 both located about a proximal side of the support base 2, and a knob 5 located at the proximal end of the support base 2. The end effector 11 is actuated and fired by the trigger 3 and the knob 5 so that the end effector 11 can staple the clamped tissue. FIG. 2 shows the stapler 1 in an unactuated open position, and FIG. 3 shows the stapler 1 in an actuated closed position after staples have been ejected to staple the tissue.

The components of the stapler 1 will be described in detail with reference to the appended drawings.

As shown in FIGS. 1 and 2, the end effector 11 is located at the distal end of the support base 2 and has a substantially U-shaped supporting structure 12 connected with the support base 2. The U-shaped supporting structure 12 can be formed by extrusion, for example, of aluminum, with subsequent machining to create the supporting structure 12. In this way, multiple parts are not required and the associated cost of manufacture and assembly is substantially reduced. In addition, the overall stability is enhanced and the stapler 1 can easily be sterilized since cobalt irradiation will effectively penetrate the extruded aluminum. Moreover, extrusion can form a smooth outer surface, which will cause less trauma to tissue. The U-shaped supporting structure 12 supports a fixed jaw 6 and a movable jaw 8. The fixed jaw 6 in turn supports an anvil 7. The movable jaw 8 contains a cartridge 9 for accommodating surgical staples. A retaining pin 10 is supported on an upper portion of the support base 2. As shown in the figures, the retaining pin 10 extends through a through hole 43 and a through hole 27 in an upper end of the movable jaw 8. The retaining pin 10 is shiftable forwardly (i.e., distally) to a hole 71 in the anvil 7 to assure that the anvil 7 and the cartridge 9 are properly aligned and the tissue captured therebetween is appropriately maintained.

Figure 4:
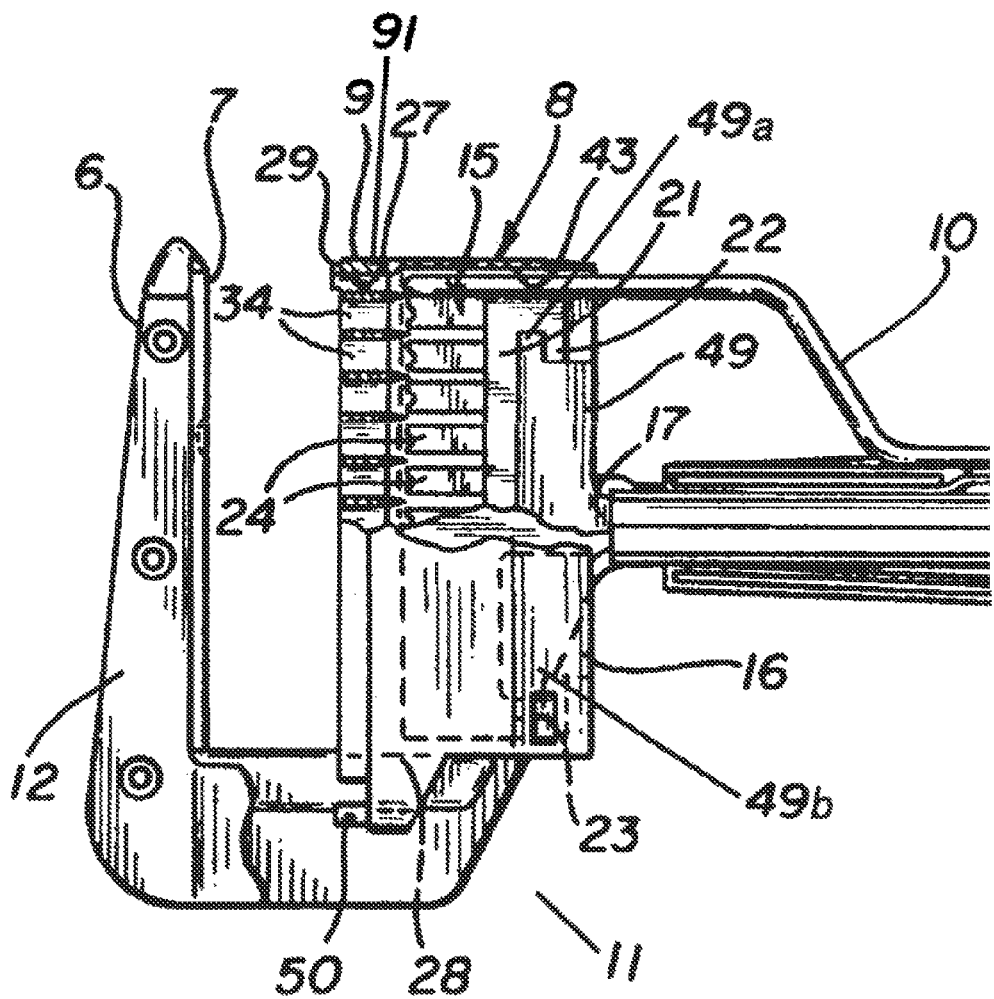
FIG. 4 is a partial cross sectional view of an end effector of the linear stapler of FIG. 1.

Reference is now made to FIG. 4, wherein the movable jaw 8 and a cartridge assembly are illustrated in a cut-out in portion sectional view. The cartridge assembly comprises the cartridge 9 facing the anvil 7, a staple driver 15 proximal to the cartridge 9, a push rod 17 extending from the proximal side to the distal side, and a casing 16 surrounding the cartridge 9, the driver 15 and a part of the push rod 17.

The cartridge 9 comprises a cartridge body 91 which may be made of polymer. The cartridge body 91 is formed with staple slots 34 for accommodating staples and also includes a cartridge lockout. Each staple slot 34 is provided at its ends with additional grooves intended to frictionally receive the legs of a surgical staple. The cartridge lockout can prevent a spent or used cartridge from being refired or reloaded after being fired. The cartridge lockout will be explained in detail below.

Immediately proximal to the cartridge 9 is disposed the driver 15. The driver 15 is molded, for example, of appropriate plastic materials having enough strength to be used in a surgical environment, and preferably made from those plastic materials which can be sterilized by known methods. The driver 15 is an integral, one-piece element comprising an elongated bracket 21, a plurality of tines 24 extending forwardly from a distal surface of the elongated bracket 21, and hook-like portions 22 and 23 extending proximally from an upper end and a lower end of a proximal surface of the elongated bracket 21. The tines 24 are equal in number to the number of staples housed in the cartridge 9. The forwardly extending tines 24 are arranged in two parallel, spaced rows, with the tines of one row staggered with respect to the tines of the other.

The lower end of the cartridge 9 is formed with a slot 28 for guiding function. The distal surface of cartridge 9 (i.e., that surface facing the anvil) is provided with a forwardly extending spacer element 29 adjacent the through hole 27 and a forwardly extending spacer 50 adjacent the outermost end of the slot 28. These spacers cooperate with the anvil to determine the distalmost position of cartridge 9.

As shown in FIG. 4, the tines 24 of the driver 15 are insertable within the staple slots 34 of the cartridge 9. It will be appreciated that the tine 24 of the driver overlies a crown of a corresponding staple. In this way, when the driver 15 is shifted distally relative to the cartridge 9, it pushes to eject the surgical staple distally out of its staple slot 34.

FIG. 4 also shows the casing 16. The casing 16, like the driver 15 and the cartridge 9, is an integral, one-piece, molded plastic member. The driver 15 is shiftably mounted within the casing 16.

The general structure of the stapler according to the one embodiment of the present invention has been described with reference to FIGS. 1-4. The above general structure description is also applicable to other embodiments of the present invention, and therefore the same will not be recited again in other embodiments.

Figure 5:
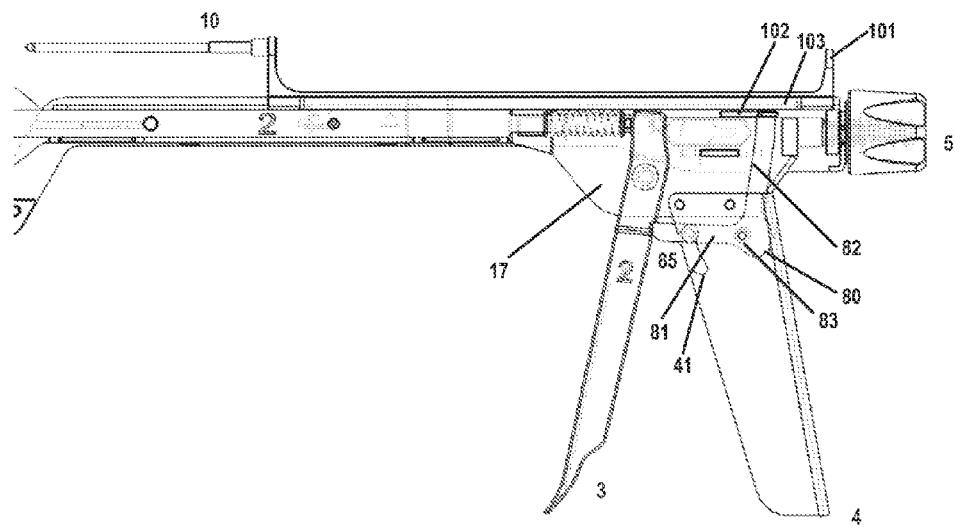
FIG. 5 is a view of a unit lockout located at a handle of the linear stapler according to another embodiment of the present invention.

FIG. 5 shows a view of the stapler according to another embodiment of the present invention, in which some parts are omitted for clarity. As shown in FIG. 5, a proximal end of the push rod 17 is associated with the trigger 3 and the knob 5. Rotation of the knob 5 moves the push rod 17 distally and rotation of the trigger 3 towards the handle 4 (indicated by an arrow D in FIG. 3) fires the cartridge 9, causing the push rod 17 to drive the driver 15 for forming the staples. A distal end of the push rod 17 terminates in a plate-like structure 49 having upper and lower lugs 49a and 49b at upper and lower side surfaces of its distal end. The plate-like structure 49 of the push rod 17 is located within the casing 16 with its upper and lower lugs 49a and 49b just nicely engaged respectively with the hook-like portions 22 and 23 of the driver 15. A distal end of the plate-like structure 49 of the push rod 17 abuts against the elongated bracket 21 of the driver 15. Thus, the distal end of the push rod 17 is locked into engagement with the driver 15 and when the push rod 17 is shifted in a distal direction, it will shift the driver 15 distally.

As shown in FIGS. 1, 2 and 4, the retaining pin 10 is in its normal, retracted position. In this retracted position, the retaining pin 10 is located within the casing 16, passing through the hole 43 in the casing 16. Once the tissue to be stapled is located between the fixed jaw 6 and the movable jaw 8, the retaining pin 10 is moved forwardly by its push button 101 located at a proximal upper portion of the support base 2. This causes the distal end of the retaining pin 10 to pass through the through hole 27 in cartridge 9, and enter into the hole 71 in the anvil 7. In its extended position, the retaining pin 10 accomplishes two purposes. First, it assures proper alignment of anvil 7 and cartridge 9 so that the staples will be properly aligned with and bent by anvil pockets when the stapler is actuated. Furthermore, the retaining pin 10 spans the distance between the fixed jaw 6 and the movable jaw 8 (i.e., between the cartridge 9 and the anvil 7), assuring that tissue located therebetween will remain in position during operation of the stapler. The push button 101 is provided with a connect cover plate 103 for indicating whether the retaining pin 10 is advanced distally an appropriate distance to align the anvil 7 and cartridge 9 and maintain the tissue there.

An advantage of the present invention is to provide a unit lockout for preventing the user from actuating the trigger 3 when the retaining pin 10 is not properly in position. As shown in FIG. 5, the stapler 1 comprises a unit lockout 80 arranged at an upper end of the handle 4. The unit lockout 80 shown in FIG. 5 is in a substantially L shape and capable of rotating around a pivot 83 at a corner portion of the L shape. The pivot 83 is fixed at the upper end of the handle 4. More specifically, in that embodiment, the unit lockout 80 comprises a horizontal lever 81 and a vertical lever 82 rigidly joined at a fixed angle and pivotable (or rotatable) around a pivot 83 at their joint. Preferably the fixed angle is about 90°. When at a lockout position, the vertical lever 82 extends upwards to about below the push button 101 of the retaining pin 10 such that the vertical lever 82 has its upper end abutting against a proximal part of the under surface of the connect cover plate of the retaining pin 10. In this lock-out position where the retaining pin 10 is not moved distally, the rotation of the vertical lever 82 is prevented. At this point, a distal end of the horizontal lever 81 is abutting against a proximal surface of the trigger 3 so that the firing movement of the trigger 3 towards the handle 4 is blocked. Only when the retaining pin 10 is pushed distally to the appropriate position by the push button 101, the vertical lever 82 is free to rotate around the pivot 83 freely. In other words, if the retaining pin 10 is not moved distally to the appropriate position (i.e., not properly aligning and maintaining the tissue), the connect cover plate 103 blocks the vertical lever 82 of the unit lockout 80 and prevents the unit lockout 80 from rotating. The horizontal lever 81 of the unit lockout 80 still abuts against the proximal surface of the trigger 3, and the trigger 3 can not be fired.

Preferably, the horizontal lever 81 has a lockout knob 85 at a position adjacent its distal end. Meanwhile, the handle 4 is formed with a groove 41 in an upper portion at the side facing the trigger 3 (i.e., the upper portion of the distal surface). When the retaining pin 10 is moved distally and the unit lockout 80 is allowed to rotate (i.e., the horizontal lever 81 is allowed to rotate about the pivot 83), the lockout knob 85 is slid downward in the groove 41 by the user to assist in rotating the unit lockout 80. With a unit lockout 80 of the above-described structure, inadvertent firing of the stapler 1 can be prevented when the anvil 7 and cartridge 9 are not properly aligned and the tissue is not maintained appropriately between them.

Figure 6:
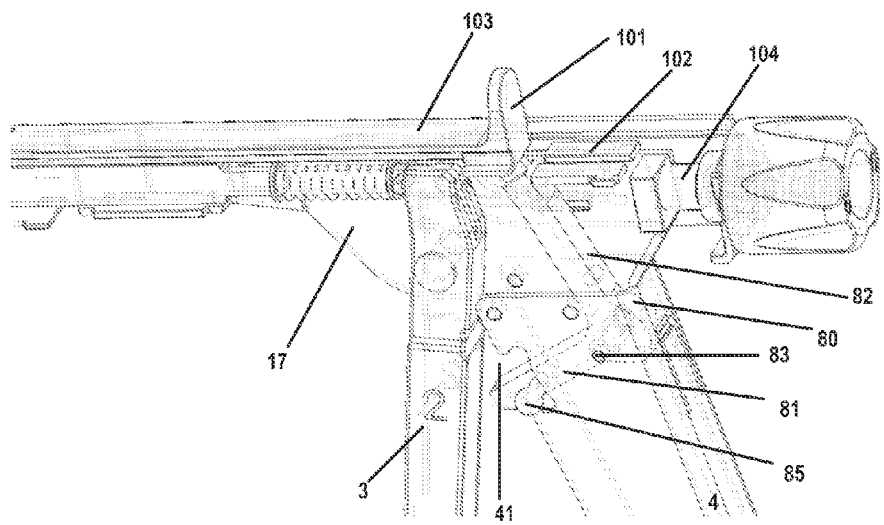
FIG. 6 is a partial perspective view of the unit lockout shown in FIG. 6 in a locked state.
Figure 7D:
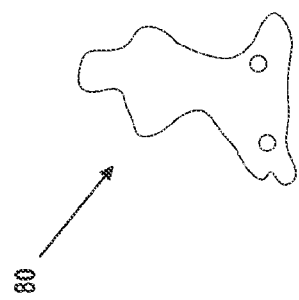
FIG. 7A to 7D are schematic views of different forms of the unit lockout located at the handle of the linear stapler.
Figure 7C:
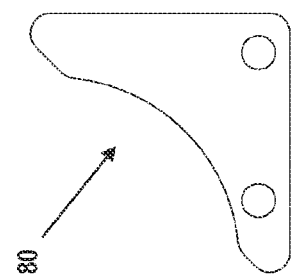
Figure 7B:
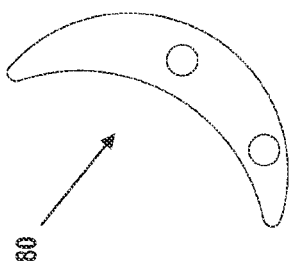
Figure 7A:
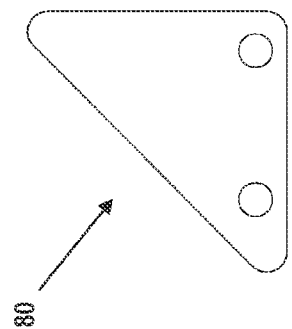

The connect cover plate 103 covers part of the support base of the stapler, as shown in FIG. 5 and FIG. 6. In the embodiment of FIG. 5, the proximal end of the retaining pin is connected to the connect cover plate 103 rigidly but is off set upward from the connect cover plate by a short distance (about 1 cm to 10 cm) to provide space for the staple cartridge.

FIG. 6 shows the unit lockout 80 is slightly rotated after the retaining pin 10 is moved to the appropriate position by the push button 101. At this point, the upper end of the vertical lever 82 of the unit lockout 80 does not abut against the downward surface about the proximal end of the connect cover plate 103. The user can push down the push knob 85 along the groove 41, which causes the distal end surface of the horizontal lever 81 of the unit lockout 80 not to abut against the proximal surface of the trigger 3 any more, permitting the user to rotate the trigger 3 towards the handle 4. Then the cartridge 9 can be fired to staple the tissue with staples.

While the unit lockout 80 has been described with reference to FIGS. 5 and 6, those skilled in the art can appreciate that the shape of the unit lockout 80 is not limited to the structure described above. FIGS. 7A to 7D show examples of different forms of the unit lockout 80. The unit lockout 80 may be in a triangle shape with blunt corners (FIG. 7A), a crescent shape (FIG. 7B), a gusset shape (FIG. 7C), or even an irregular shape (FIG. 7D) as long as the shape includes two ends that extend from a pivot with an angle between them. Preferably the angle between the two ends extending from the pivot is about 30°-150°, more preferably about 60° to 120°, more preferably about 80° to 100°. Any suitable shape of the unit lockout 80 is feasible as long as the upper end of the unit lockout 80 can abut against the connect cover plate 103, the distal end thereof can abut against the proximal surface of the trigger at the same time, and the unit lockout 80 can rotate around the pivot at proximal side when nothing is blocking its pivotal movement. With this arrangement the unit lockout 80 can lock the trigger 3 at one position and allow the trigger 3 to be actuated when rotated to a different position.

The unit lockout 80 may be made of polymer or metal as long as it can be sterilized in the reconditioned process.

In an embodiment shown in FIGS. 5 and 6, the support base of the stapler has at least one range lockout plate 102 rigidly affixed to it in a longitudinal (in a proximal to distal orientation) manner such that in a lockout position it is near and above the upper end of the unit lockout 80 thereby blocking the upper end of the unit lockout 80 from moving freely upward when the stapler is in a lockout position. The unit lockout 80 and the handle are movable longitudinally relative to the range lockout plate(s) 102. In this way, the range lockout plate(s) 102 can prevent the rotation (or pivoting) of the unit lockout 80 about the pivot 83 when the staple unit lockout 80 has not been moved distally yet. Preferably there are two range lockout plates as shown in FIG. 7 both blocking the upward movement of the upper end of the unit lockout 80. Knob 5 is in screw thread relation with handle shaft 104 which is operatively connected to handle 4 so that rotation of the knob 5 will move the handle shaft 104 and handle 4 longitudinally relative to range lockout plate(s) 102, thereby moving the unit lockout 80 relative to the range lockout plate(s) 102. By rotating knob 5, the upper end of the unit lockout 80 can be moved to a position of no longer underneath the range lockout plate(s) 102, such that the range lockout plate(s) 102 no longer blocks an upward movement of the upper end of the unit lockout 80. The movable jaw 8, and handle 4 are operatively connected together such that rotation of the knob 5 will also move the movable jaw 8 for positioning the staple cartridge near the tissue. Before firing the stapler, the user can move the movable jaw 8, handle 4 and the unit lockout 80 distally relative to the fixed jaw 6 and the range lockout plate(s) 102 on support base 2. Thus, the unit lockout 80 can perform two lockout functions, one by preventing free pivoting in conjunction with the range lockout plate(s) 102 and one by preventing free pivoting in conjunction with the connect cover plate 103, which is connected to the retaining pin. When neither the connect cover plate nor the range lockout plate 102 are above and blocking the upward movement of the upper end of lockout 80, the lockout 80 can be pivoted to unlock the trigger 3, thereby allowing the trigger 3 to be freely pressed to fire a staple. Thus, either the range lockout plate(s) 102 or the connect cover plate connected to the retaining pin can function as a blocking plate to block the pivoting of the unit lockout 80, depending on their positions whether they are in the way of the upper end of the unit blockout 80. When the stapler is in a complete lockout position, both the range lockout plate(s) 102 and the connect cover plate are in the way of upward movement of the upper end of the unit lockout.

Figure 8:
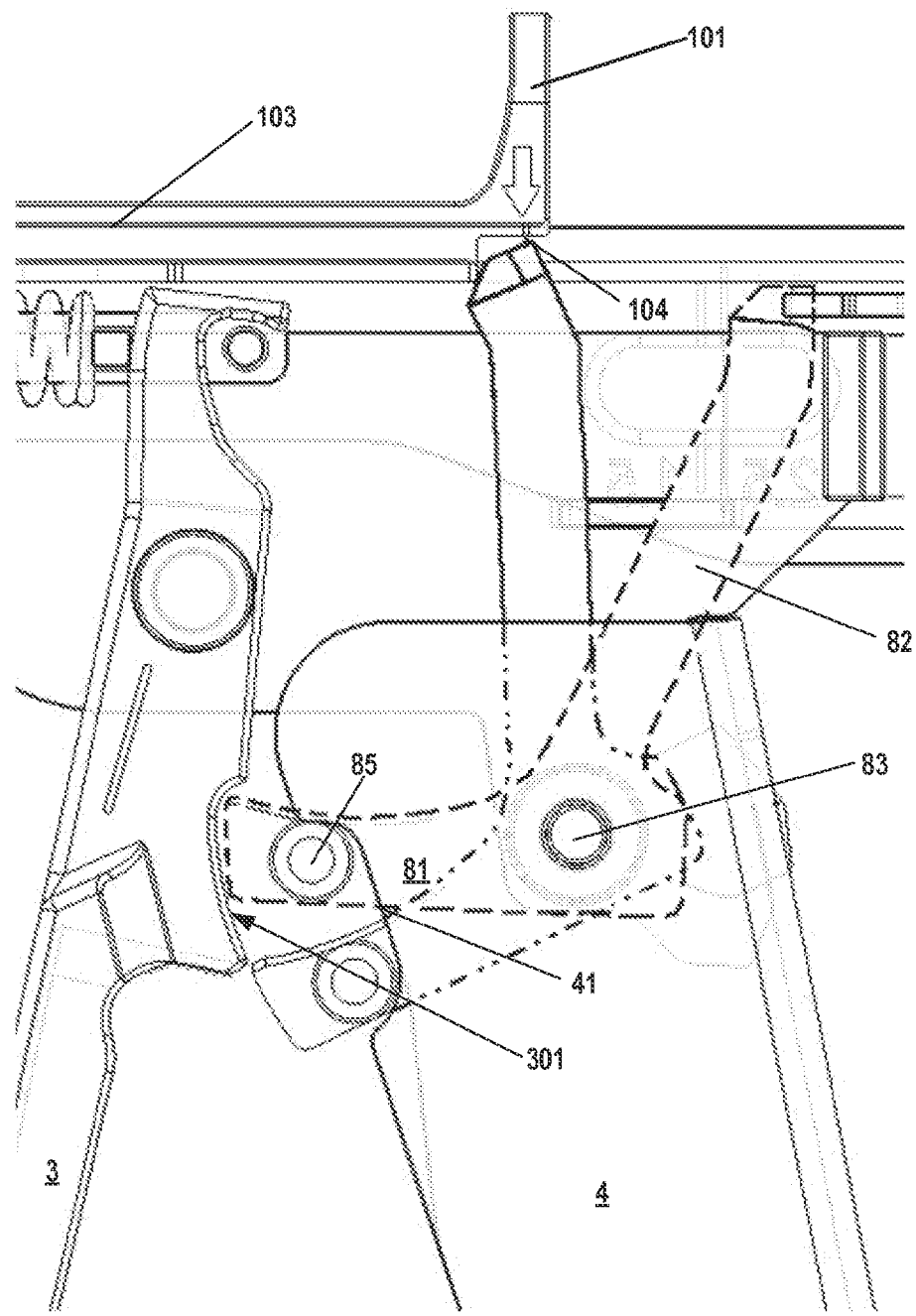
FIG. 8 is yet another embodiment of the unit lockout located at the handle of the linear stapler, showing simultaneously a locked state in which a distal end of a horizontal lever of the unit lockout abuts against a trigger and an unlocked state in which the horizontal lever is away from the trigger.

FIG. 8 is another embodiment of the unit lockout located at the handle of the linear stapler, showing simultaneously a locked state in which the distal end of the horizontal lever of the unit lockout abuts against the trigger and an unlocked state in which the horizontal lever is away from the trigger. The differences between the present embodiment and the above embodiment lie in that the upper portion of the proximal side of the trigger 3 has a concave arc-shaped lockout profile 301, and a recess portion 104 is formed at the proximal end of the retaining pin 10 under the push button 101.

In the embodiment, in the locked state, the vertical lever 82 of the unit lockout 80 is blocked by the lower surface of the connect cover plate 103, the distal end of the horizontal lever 81 abuts against the lockout profile 301 of the trigger 3, so that the horizontal lever 81 and the vertical lever 82 are prevented from rotating, thereby the trigger 3 is prevented from firing. As stated above, the retaining pin 10 is shiftable forwardly (i.e., distally) to the hole 71 in the anvil 7 to assure that the anvil 7 and the cartridge 9 are properly aligned and the tissue captured therebetween is appropriately maintained. In such cases, it is necessary to make sure that the retaining pin 10 is properly inserted into the hole 71 of the anvil 7. Problems will arise if the retaining pin 10 is shifted distally by the push button 101 but is not properly positioned. In the embodiment, the lockout profile 301 has a length to allow the distal end of the horizontal lever 81 to move thereon when the horizontal lever 81 is rotated. Therefore, when the distal end of the retaining pin 10 is moved distally but not inserted into the hole 71 of the anvil 7 yet, the horizontal lever 81 and the vertical lever 82 of the unit lockout 80 are rotated but not rotated beyond a threshold angle (such as 27.8 degrees) corresponding to the length of the lockout profile 301. Within the range of the threshold angle, the lockout profile 301 holds the distal end of the horizontal lever 81, so that the stapler 1 cannot be fired. If the operator still wants to fire the stapler 1, he or she may make the lockout knob 85 slide downward along the groove 41 to assist in rotating the horizontal lever 81 and the vertical lever 82 of the unit lockout 80 beyond the threshold angle, such as 27.8 degrees up to 30 degrees. At this point, the upper end of the vertical lever 82 engages with the recess portion 104 at the proximal end of the retaining pin 10. Rotating the horizontal lever 81 continuously, the upper end of the vertical lever 82 will push the distal end of the retaining pin 10 into the hole 71 of the anvil, so that the stapler 1 can be fired.

The various embodiments of the present invention have been described above in connection with linear staplers. It should be noted, however, that in other embodiments, the inventive surgical instrument disclosed herein need not to be a linear stapler, but may be a curved stapler, round stapler, and the like, and even a stapler of an irregular shape. The present invention also has application in conventional endoscopic and open surgical instrumentation as well as robotic-assisted surgery.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can be done using a variety of techniques for disassembly, cleaning/replacement, and reassembly. Use of such techniques, and the resulting reconditioned instrument, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

The invention claimed is:

1. A surgical stapler, comprising:
   a support base;
   a trigger located at a proximal end of the support base;
   a handle located at a proximal end of the support base;
   a retaining pin operatively connected to and extending distally from a support base, the support base being operable in the surgical stapler to cause the stapler to position staples near tissue; and
   a unit lockout rotatable about a pivot fixed to the handle, the unit lockout comprising:
      an upper end near and under at least one blocking plate in the stapler; and
      another end facing the trigger to prevent it from firing when the upper end is blocked from upward movement by the at least one blocking plate,
   whereas the upper end of the unit lockout is moved relative to the at least one blocking plate so that the upper end of unit lockout is no longer under the at least one blocking plate to permit the unit lockout to rotate about the pivot.

2. The surgical stapler of claim 1, wherein the at least one blocking plate comprises a connect cover plate from which the retaining pin is rigidly connected and extended distally, wherein when the retaining pin is not moved distally the connect cover plate blocks the upper end of the unit lockout from moving upward freely.

3. The surgical stapler of claim 1, wherein the at least one blocking plate comprises at least one lockout plate rigidly connected to a support base movable relative to the handle, the upper end of the unit lockout being movable relative to the lockout plate.

4. The surgical stapler of claim 1, wherein the at least one blocking plate comprises a connect cover plate from which the retaining pin is rigidly connected and extending distally wherein when the retaining pin is not moved distally the connect cover plate blocks the upper end of the unit lockout from moving upward freely and the at least one blocking plate further comprises at least one lockout plate rigidly connected to a support base which is movable relative to the handle.

5. The surgical stapler of claim 1, wherein the unit lockout further comprises a lockout knob located adjacent the another end and capable of being slid downwards in a groove formed in an upper portion of the proximal surface of the handle by a user when the retaining pin is moved distally and the upper end is not blocked from upward movement by the at least one blocking plate, so that the unit lockout can be rotated, allowing the trigger to be rotated towards the handle.

6. The surgical stapler of claim 1, wherein the unit lockout is in an L shape, a blunt triangle shape, a crescent shape, or a gusset shape.

7. The surgical stapler of claim 1, wherein the unit lockout is made of metal or polymer.

8. The surgical stapler of claim 1, wherein the retaining pin extends in a direction about parallel to the direction of slide of a connect cover plate rigidly connected to the retaining pin slidable on the support base but is off set upward from the slidable connect cover plate by 1 cm to 10 cm.

9. The surgical stapler of claim 1, wherein the pivot is located at an upper portion of the handle.

10. The surgical stapler of claim 1, wherein the retaining pin is connected to a push button via a connect cover plate operatively.

11. The surgical stapler of claim 1, wherein when the retaining pin is shifted distally but not properly positioned yet, the unit lockout is rotated an angle smaller than a threshold angle and the trigger cannot be fired, when the unit lockout is rotated continuously as desired by the operator and beyond the threshold angle, the upper end will push the retaining pin to position it properly, so that the trigger can be fired.

* * * * *